United States Patent [19]
Lowell

[11] Patent Number: 5,902,107
[45] Date of Patent: *May 11, 1999

[54] DISPOSABLE PROPHYLAXIS ANGLE WITH ADJUSTABLE HEAD

[76] Inventor: Jeremy Lowell, 4421 Dale Blvd., Woodbridge, Va. 22193

[21] Appl. No.: 08/955,488

[22] Filed: Oct. 22, 1997

Related U.S. Application Data

[60] Provisional application No. 60/030,912, Nov. 14, 1996.

[51] Int. Cl.⁶ .................................................. A61C 1/12
[52] U.S. Cl. ........................... 433/130; 433/112; 433/125
[58] Field of Search ................................. 473/130, 112, 473/124, 125

[56] References Cited

U.S. PATENT DOCUMENTS

| | | | |
|---|---|---|---|
| 604,836 | 5/1898 | McDonald | 433/112 |
| 1,170,524 | 2/1916 | Fernald | 433/130 |
| 1,379,880 | 5/1921 | Seaborn | 433/130 |
| 3,409,224 | 11/1968 | Harp et al. | 239/33 |
| 3,472,045 | 10/1969 | Nelsen et al. | 433/125 |
| 5,052,071 | 10/1991 | Halm | 15/167.1 |
| 5,054,154 | 10/1991 | Schiffer et al. | 15/167.1 |
| 5,114,074 | 5/1992 | Fraunthal et al. | 239/33 |
| 5,150,495 | 9/1992 | Discko et al. | 15/167.1 |
| 5,156,547 | 10/1992 | Bailey | 433/125 |
| 5,423,679 | 6/1995 | Bailey | 433/125 |
| 5,433,605 | 7/1995 | Strobl, Jr. | 433/112 |
| 5,476,630 | 12/1995 | Orsing | 264/508 |

FOREIGN PATENT DOCUMENTS

| | | | |
|---|---|---|---|
| 433773 | 6/1991 | European Pat. Off. . | |
| 2225122 | 11/1974 | France . | |
| 1027362 | 4/1958 | Germany | 433/130 |
| 1806530 | 5/1970 | Germany . | |
| 2533948 | 2/1977 | Germany | 433/112 |
| 218792 | 5/1923 | United Kingdom . | |
| 2209284 | 5/1989 | United Kingdom . | |

*Primary Examiner*—John J. Wilson
*Attorney, Agent, or Firm*—Richard C. Litman

[57] ABSTRACT

A disposable prophylaxis angle with an adjustable head having a body with a head, a drive gear extending through the body, and a driven gear extending through the head. The prophylaxis angle includes a body which has a portion thereof formed from a plurality of accordion folds for selective angular adjustment of the body. The drive gear includes a gear portion and a shaft portion for journaled rotation within the body. The driven gear includes a shaft portion mounted for journaled rotation within the head bore, and a gear portion operatively connected to the gear portion of the drive gear. The plurality of annular accordion folds allow for adjustment of the body in any radial direction. The shaft portion of the drive gear accommodates the angular adjustment of the prophylaxis angle by maintaining the operative connection between the gear part of the drive gear and the gear part of the driven gear. To accommodate the selected angular adjustment, the shaft portion of the drive gear comprises either: (1) a reduced diameter portion which allows the shaft to flex over a portion of its length, or (2) a shaft portion including a lower shaft part and an upper shaft part which are connected at a universal joint.

3 Claims, 4 Drawing Sheets

DISPOSABLE PROPHYLAXIS ANGLE WITH ADJUSTABLE HEAD

CROSS-REFERENCE TO RELATED APPLICATION

This application claims the benefit of U.S. Provisional Patent Application Ser. No. 60/030,912, filed Nov. 14, 1996.

BACKGROUND OF THE INVENTION

1. Field of the Invention

The present invention relates to dental or prophylaxis angles and, more specifically, to a disposable dental angle. Even more specifically, the present invention relates to a disposable dental angle having an angularly adjustable head.

2. Description of the Prior Art

Dental angles carry dental bits such as prophy cups and brushes, and burs. The angle enables dentists and hygienists more easily to reach the various surfaces of a patient's teeth. These angles generally include a body having a head thereon which has an axis that is angularly positioned with respect to an axis of the body. Typically, the angle of separation between the head and the body is 90°. A drive gear and driven gear are supported within the body for enmeshing engagement to cause rotation of a dental bit that is carried by the driven gear. The body is normally slipped over the nose of a handpiece, such as a Doroit type handpiece, which has a collet that receives a shaft of the drive gear. The collet holds the shaft and connects the same to a motor which, upon operation, causes rotation of the shaft and the drive gear, and thus the driven gear with the dental bit.

Contra-angles are also used to carry dental bits; however, the contra-angles are particularly disposed for use in reaching difficult spots in a patient's mouth. Typically, the axis of the head is angled anywhere from 100° to 120° with respect to the axis of the body. To drive the driven gear that carries the dental bit, it is well known to use two drive shafts, one of which connects to the collet and the other of which connects to the driven gear. The two drive shafts are connected by intermediate gears that impart rotation to the driven gear upon rotation of the collet. Non-disposable contra-angles typically are quite complex and expensive; however, the prior art contains two examples of disposable contra-angles.

U.S. Pat. No. 5,423,679, which issued to Ronald L. Bailey on Jun. 13, 1995, discloses in one embodiment a disposable prophylaxis contra-angle. The disposable prophylaxis contra-angle has a plastic body with its head fixed at an angular position which is about 15° from the normal position. A one piece drive shaft and gear is made of a thermoplastic material, with a portion of the shaft being hollow to allow the shaft to bend as it rotates.

Another disposable contra-angle is disclosed in U.S. Pat. No. 5,433,605, which issued to Frederick P. Strobl, Jr., on Jul. 18, 1995. The disposable contra-angle has a body composed of two body components which are rotatably connected together with their respective axes offset by an angle of approximately 8°–12°. The first body component is disposed to attach to a collet of a drive unit, and the second body component rotatably attaches to the first body component for 360° rotation thereon. Thus, while the angle of inclination is fixed, the angle is adjustable to a limited extent (i.e., ±8°–12°). A flexible drive shaft extends through the first and second components for driving a driven element and a dental bit. The drive shaft is made of a resilient thermoplastic material, and the shaft has a reduced diameter portion that allows the shaft to flex to the extent required. Furthermore, it is necessary for the thermoplastic material to have a tensile strength that exceeds the tensile stresses placed on the stretched side of the shaft.

Each of the above pieces of prior art utilize contra-angles which have a fixed angle of inclination. While the Strobl, Jr., device offers some adjustability by virtue of the rotatable connection, it does not offer an infinitely variable angle adjustment. Thus, the above contra-angles cannot possibly have a standard 90° angle head position.

Other dental utensils have, however, been prepared so that they are capable of infinitely variable adjustments. One such device is disclosed in U.S. Pat. No. 5,150,495, which issued to Discko, Jr., et al. on Sep. 29, 1992. The device disclosed therein is a disposable bendable dental brush which has a bendable portion that comprises accordion-like folds. The accordion-like folds are rigid enough to allow the brush to be bent into an angular position, whereby the brush maintains the angular position until it is readjusted.

None of the above inventions and patents, taken either singly or in combination, is seen to describe the instant invention as claimed.

SUMMARY OF THE INVENTION

A disposable prophylaxis angle of the present invention has a flexible body and drive shaft to provide an adjustable head. The prophylaxis angle comprises a body that connects to a powered handpiece, such as a Doroit handpiece, for powered rotation of a drive gear and driven gear to cause rotation of a dental bit such as a prophy cup. The body is preferably an integral one-piece body having a sleeve portion for connecting to the powered handpiece, a lower neck portion for angular adjustment of the prophylaxis angle, an upper neck portion, and a head portion. The sleeve portion has an axial sleeve bore extending therethrough which communicates with a passageway through the lower neck portion. The upper neck portion has an axial upper neck bore extending therethrough which communicates with the passageway of the lower neck portion. Connected to the upper neck portion is a head which has an axial head bore that is perpendicularly aligned with the upper neck bore.

The drive gear includes a shaft portion which extends through the sleeve portion, lower neck portion, and upper neck portion for journaled rotation therein, and a gear portion which extends into the head bore. A driven gear includes a shaft portion mounted for journaled rotation within the head bore, and a gear portion operatively connected to the gear portion of the drive gear. The driven gear also includes means for retaining a dental bit.

Angular adjustment of the prophylaxis angle results in the angular displacement of the upper neck bore with respect to the sleeve bore. To allow for such angular adjustment, the lower neck portion is provided a plurality of annular accordion folds which allow for adjustment in any radial direction. The shaft portion of the drive gear must also accommodate the angular adjustment of the prophylaxis angle, whereby the shaft maintains the operative connection between the gear part of the drive gear and the gear part of the driven gear.

According to one embodiment, the shaft portion of the drive gear includes a reduced diameter portion which allows the shaft to flex over a length of the shaft extending between upper and lower bearing seats. The bearing seats allows the shaft portion to smoothly rotate during operation of the angle while angularly adjusted. To achieve the desired flexing of the shaft portion, it is necessary for the drive gear to be formed of a thermoplastic material which has a tensile strength greater than the tensile stresses placed upon the stretched side of the shaft during operation.

According to a second embodiment, the shaft portion of the drive gear includes a lower shaft part and an upper shaft part which are connected at a universal joint. The universal joint allows for angular displacement of the upper shaft part with respect to the lower shaft part when the lower neck portion is angularly adjusted. The universal joint is located within the passageway through the lower neck part, and specifically between upper and lower bearing seats which support the upper and lower shaft parts, respectively, for journaled rotation within the body.

Accordingly, it is a principal object of the invention to provide a disposable prophylaxis angle which has an adjustable head to allow the angle to function as both a standard 90° angle as well as a contra angle.

It is another object of the invention to provide a disposable prophylaxis angle which may be discarded following its use.

It is a further object of the invention to provide a disposable prophylaxis angle which is selectively adjustable in any direction.

Still another object of the invention is to provide a disposable prophylaxis angle with a head adjustable in any direction between 0–30°.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
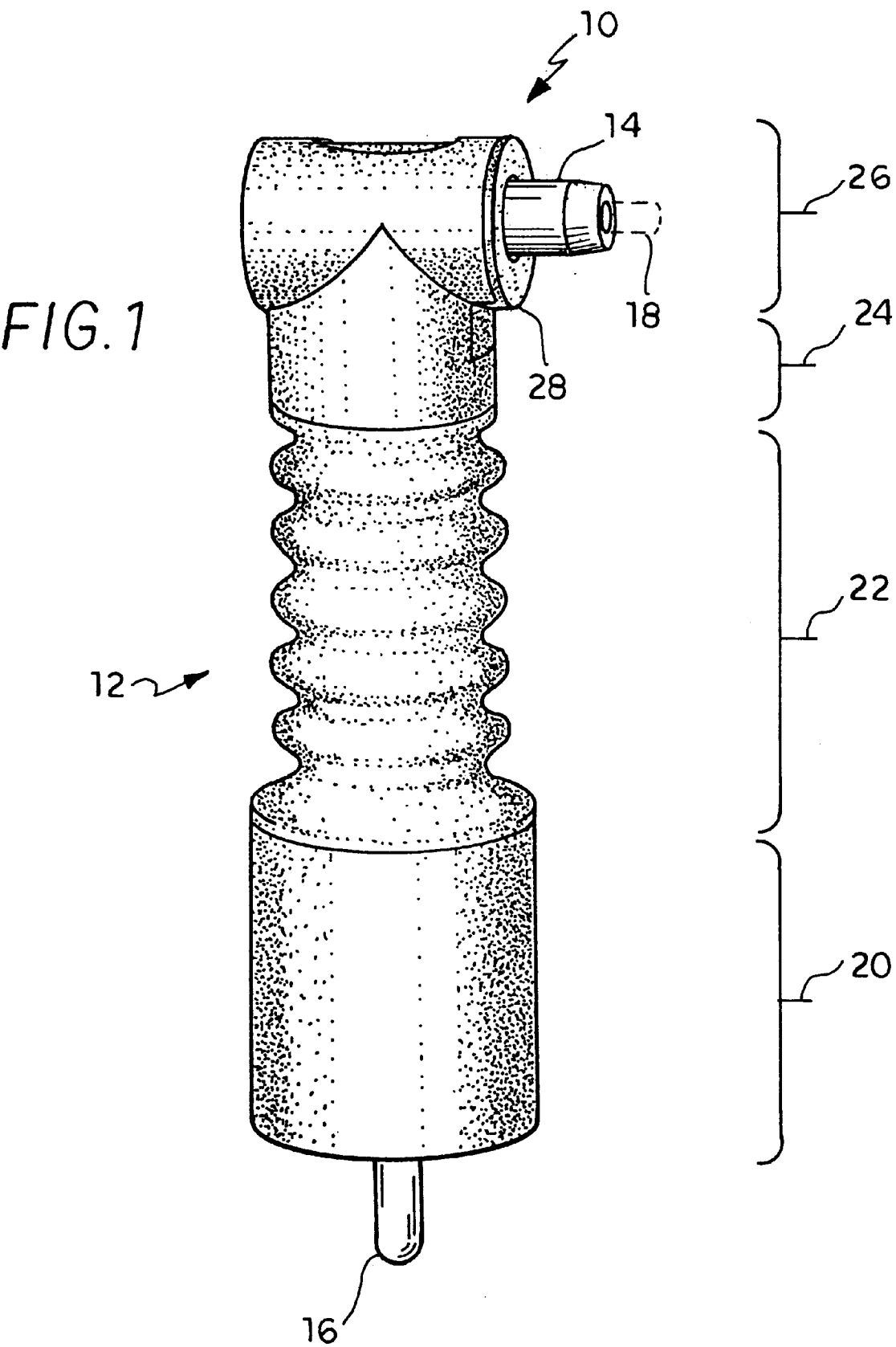
FIG. 1 is perspective view of a disposable prophylaxis angle with adjustable head according to the present invention.

Referring now to the figures by numerals of reference, and first to FIG. 1, 10 denotes generally a disposable prophylaxis angle with adjustable head according to the present invention. The prophylaxis angle 10 comprises generally a body 12, a driven gear 14, and a drive gear 16. The body 12 is formed of several distinct sections, generally denoted as a sleeve 20, a lower neck 22, an upper neck 24, and a head 26. A separable cap 28 is removably connected to the head 26, as discussed hereinafter. Preferably the above-listed sections of the body are integrally connected and formed from one or more types of a plastic material. The plastic material which forms the body and the cap should be substantially rigid. In particular, the plastic used to form the lower neck 22 should be flexible enough to allow the angle 10 to adjust, as described hereinafter, yet rigid enough to hold its position following angular adjustment. The driven gear 14 and the driving gear 16 preferably are formed of a plastic material which has a low coefficient of friction, such as a material which is self-lubricating. Thus, the plastic material which forms the body and cap should be different from the plastic material which forms the driving and driven gears.

Figure 2:
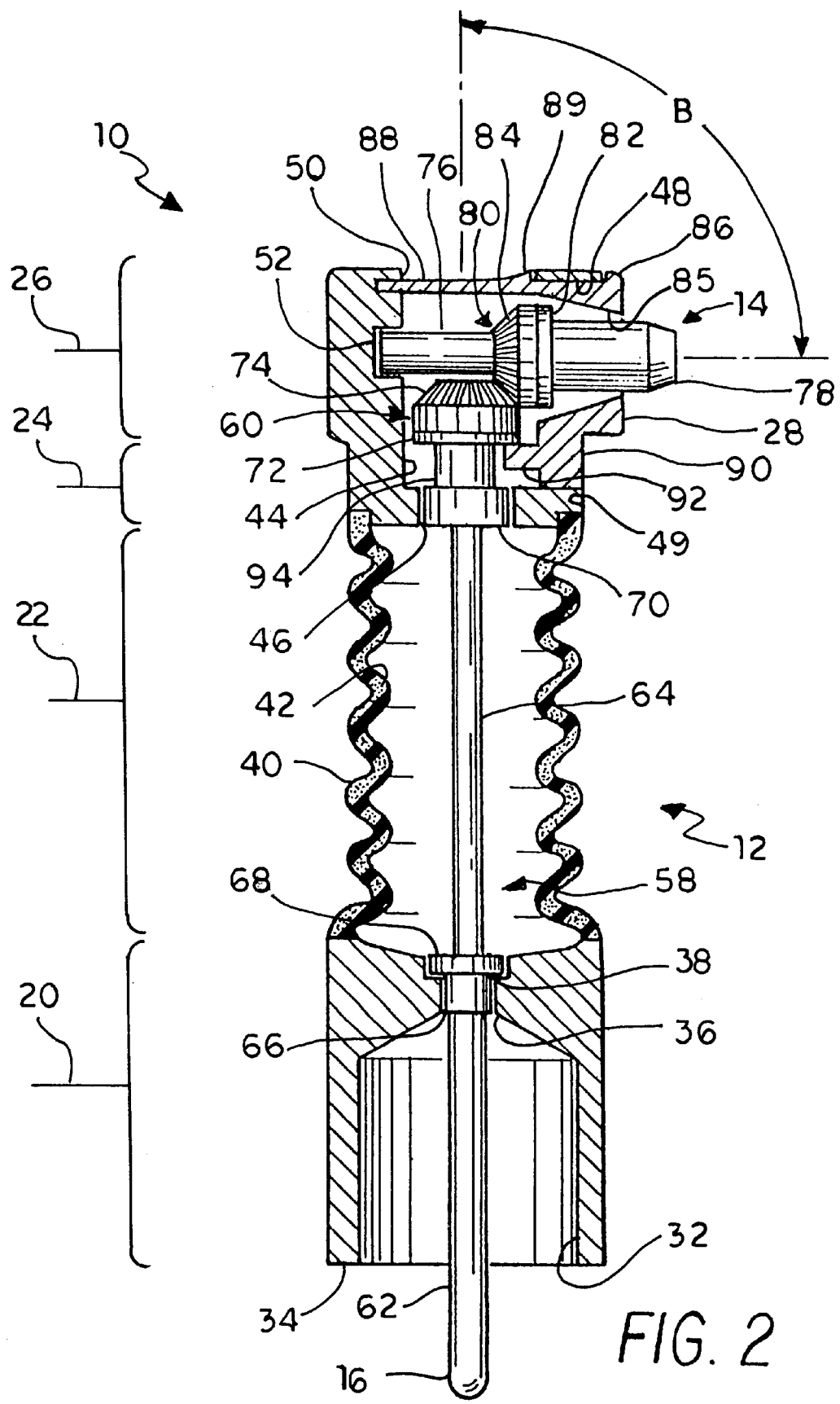
FIG. 2 is a cross sectional view of one embodiment of the invention shown with its lower neck part unadjusted so that the shaft remains straight.

Referring now to FIGS. 1 and 2, the sleeve portion 20 of the body is disposed to fit over a collet of a handpiece, such as a Doroit type handpiece, which provides the power to rotate the driving and driven gears. To receive the collet, the sleeve portion is provided with a bottom end 34 that opens to an axial sleeve bore 32. The body 12 is positioned on the handpiece through the interaction of a slot (not shown) in the sleeve 20 with an aligning pin on the handpiece. At its upper end the sleeve bore 32 tapers to a reduced diameter lower bearing seat 36 which has a shoulder 38. The reduced diameter lower bearing seat 36 acts as a journal as described hereinafter.

The sleeve portion 20 is connected to the lower neck portion 22. Although the sleeve portion and lower neck portion preferably are integrally connected, a mechanical connection also will suffice. The lower neck portion is formed of a plurality of annular accordion folds 40 that allow the lower neck portion 22 to be angularly adjusted. The lower neck portion has a passageway 42 therethrough which communicates with the sleeve bore 32.

The lower neck portion 22 is connected to the upper neck portion 24. Like the connection between the sleeve portion and the lower neck portion, this also is preferably an integral connection; however, as before, a mechanical connection also will suffice. The upper neck portion 24 has an axial upper neck bore 44 which communicates with the passageway 42 of the lower neck portion. Where upper neck bore 44 communicates with the passageway 42, the upper neck bore has a reduced diameter upper bearing seat 46 which acts as a journal as described hereinafter. The alignment of the upper neck bore 44 and the sleeve bore 32 may be adjusted so that they are coaxial. Due to the adjustable nature of the lower neck portion, however, the upper neck bore 44 is disposed selectively to be angularly displaced from the sleeve bore 32.

The upper neck portion 24 is integrally connected to the head portion 26. The head portion is generally barrel shaped and has an axial head bore 48 which is angularly offset from the upper neck bore 44. The head bore 48 preferably is formed at an angle β to the upper neck bore 44, which preferably is 90°. At its top, head 26 has an aperture 50 which is wide enough to allow insertion of the drive gear 16 through the aperture and into the body 12. Internal to the head and located at its back side is a recess 52 which is coaxial with the head bore 48. At the front side of head portion 26 is an enlarged opening 49 which extends below into the upper neck portion 24.

The drive gear 16 generally comprises a shaft portion 58 and a gear portion 60. The shaft portion extends rotatably through the sleeve bore 32, the passageway 42, and the upper neck bore 44. The shaft portion includes a bottom stem 62, which is disposed to be retained by the collet of a handpiece, and a reduced diameter portion 64. The reduced diameter portion allows the shaft to bend in the region of the lower neck portion, where the body is adjustable due to the presence of the annular accordion folds 40. Intermediate the reduced diameter portion 64 and the bottom stem 62 is an enlarged diameter lower bearing 66 that has an annular flange 68 adjacent the reduced diameter portion. The lower bearing 66 contacts the lower bearing seat 36 for journaled rotation of the shaft portion at lower bearing seat 36. An enlarged upper diameter lower bearing 70 is provided at the opposite end of the reduced diameter portion 64. The upper bearing 70 contacts the upper bearing seat 46 for journaled rotation of the shaft portion at bearing seat 46. Together the interaction between the pairs of bearing seats 36, 46 and bearings 66, 70 on the shaft provide smooth rotation of the drive gear 16 within the body 12.

The gear portion 60 of the shaft is spaced apart from the upper bearing 70 such that the gear portion extends into the head bore 48. The gear portion 60 includes a planar base 72 having a plurality of radially equispaced teeth 74 extending into the head bore 48 from one side of the base. To maintain the gear portion 60 in its proper position within head bore 48 (i.e., to prevent the drive gear 16 from sliding too far towards the bottom end 31), flange 68 contacts and rests against shoulder 38. Thus, the flange 68 helps to maintain the gear portion 60 slightly below the recess 52.

The driven gear 14 is coaxially seated within the head bore 48 where it is operatively connected to the gear portion 60 of the drive gear 16 for journaled rotation within the head bore. The driven gear comprises a shaft portion 76 integrally connected to a gear portion 80 which is integral with a protruding dental bit receiving means 78. The shaft portion 76 is disposed to be seated within the recess 52 during use of the angle 10, thereby maintaining the driven gear coaxially aligned within the head bore 48. The gear portion 80 includes a planar base 82 having a plurality of radially equispaced teeth 84 which project from one side of the base 82 for enmeshing engagement with the teeth 74 of the drive gear 16.

To maintain the enmeshing engagement of the teeth on the drive gear 16 and the teeth on the driven gear 14, cap 28 is received in the head bore 48. The cap 28 generally includes an outer lip 86, and elongate cover 88 integral with the outer lip, and a lower extension 90 integral with the outer lip. The outer lip 86 defines a coaxial tapered aperture 85 through which the dental bit receiving means 78 passes following placement of the cap onto the body 12. The elongate cover 88 is disposed to extend into the head bore partially to cover the driven gear 14 and to close the aperture 50. The cover 88 extends around the sides of the driven gear 14 without interfering with the engagement between the drive gear 16 and the driven gear. To provide a snap fit between the cap 28 and the head portion 26, a contoured rib 89 is provided on the cover 88 to engage the edge of the aperture 50 when the cover is inserted into the head bore 48. The rib 89 prevents unwanted disengagement of the cap from the body, but it allows manipulated separation of the two pieces.

An arcuate rib 92 is provided on the internal edge of the lower extension 90, whereby the rib 92 fits into an annular groove 94 formed between the bearing 70 and the planar base 72 of the drive gear 16. By fitting into the annular groove 94, the rib 92 prevents extensive movement of the drive gear 16 in the direction of the driven gear 14. The effect of the rib 92 to prevent axial movement of the drive gear in one direction and the effect of the flange 68 to prevent axial movement of the drive gear in the other direction together ensure constant enmeshing engagement between the teeth 74 and 84 of the drive gear 16 and driven gear 14, respectively.

To assemble the prophylaxis angle 10 of the present invention, the drive gear 16 is inserted shaft first through the aperture 50 in the head 26. The drive gear 16 comes to rest when the flange 68 contacts shoulder 38 to prevent its axial movement in the direction of the bottom end 34. Following insertion of the drive gear, the driven gear is inserted through opening 49 until its shaft portion 76 is received within the recess 52 and the teeth 84 of driven gear 14 enmeshingly engage the teeth 74 of the driving gear 16. Finally the cap 28 is inserted into the head bore such that the contoured rib 89 snaps into position within the aperture 50 to prevent unwanted disengagement of the cap from the body.

To use the disposable prophylaxis angle 10 of the present invention, a user (i.e., dental hygienist or dentist) should place the sleeve portion 20 over the collet of the handpiece, where the bottom stem 62 of the driving gear 16 is captured by the collet. A dental bit 18, such as a prophy cup or the like, is removably attached to the driven gear 14 by inserting the bit into the dental bit receiving means 78. The dental bit may be secured to the receiving means with a threaded connection or the like. Once the bit is secured to the driven gear, the user may operate the handpiece to cause rotation of the bit as desired.

Figure 3:
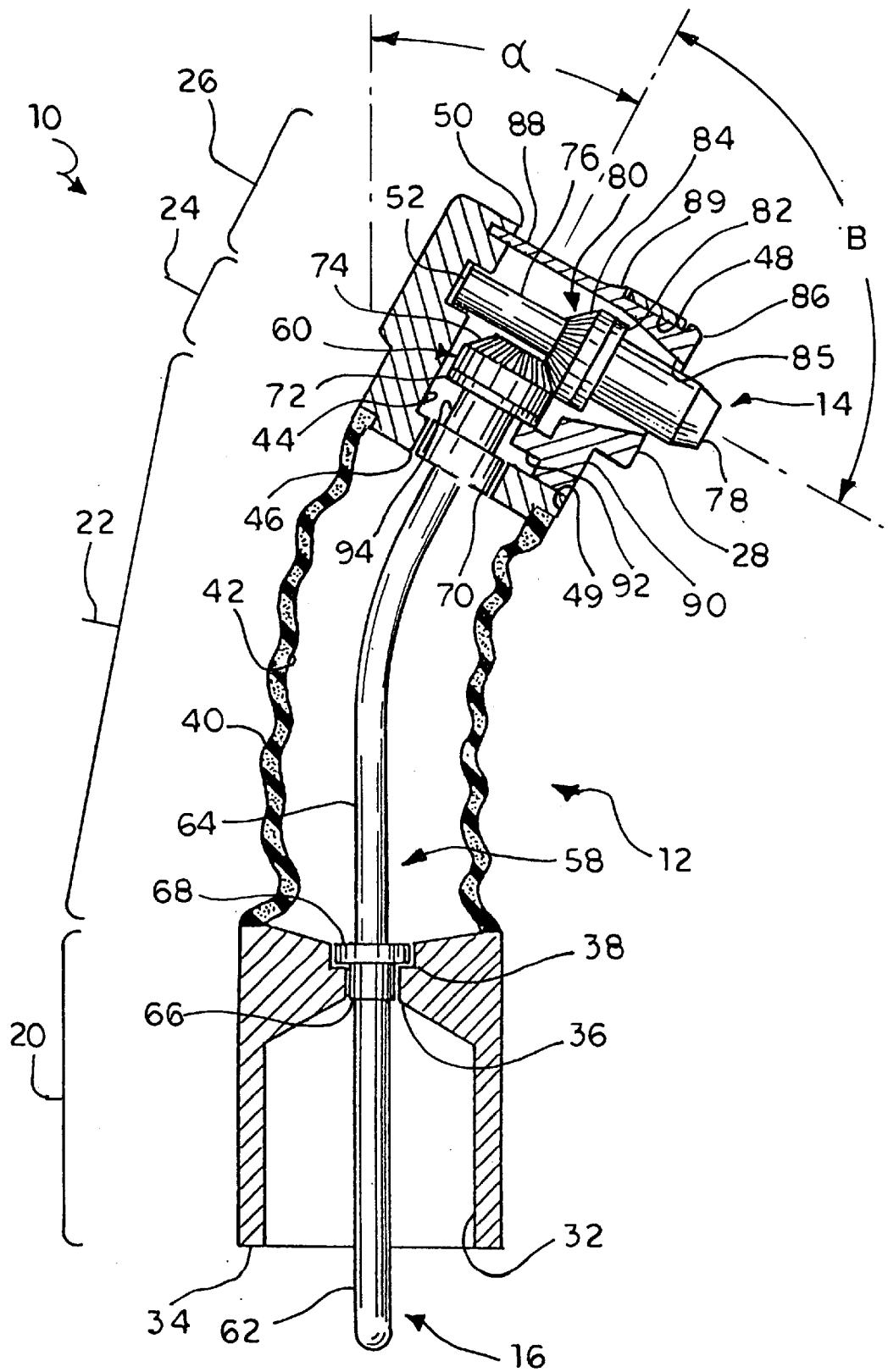
FIG. 3 is a cross sectional view of the same embodiment showing the lower neck portion adjusted by a 30° angle of displacement which causes the shaft to bend accordingly.

The lower neck portion 22 is angularly adjustable in any direction for angularly displacing the upper neck bore with respect to the sleeve bore. To allow for the desired angular adjustment, the shaft portion 58 of the drive gear accommodates the angular adjustment while maintaining the operative connection between the gear part 60 of the drive gear and the gear part 80 of the driven gear. To selectively adjust the angular displacement of the head portion 26 with respect to the sleeve portion 20, a user should press against the head portion until the desired angle of displacement $\alpha$ is achieved. An angle $\alpha$ between 0–30° may be achieved in any radial direction such as, for example (as shown in FIG. 3), the adjustment displaces the upper neck portion and head portion forward 30° with respect to the sleeve. It should be apparent, however, that the angle $\beta$ (between the head portion and the upper neck portion) does not change. When the head portion is angularly displaced, the annular accordion folds 40 allow the lower neck portion 22 to bend in any direction. Simultaneously, the reduced diameter portion 64 of the shaft portion 58 bends to accommodate the desired angle change. While the reduced diameter portion 64 bends (as shown in FIG. 3), the interaction between the pairs of bearing seats 36, 46 and bearings 66, 70 on the shaft provide smooth rotation of the drive gear 16 within the body 12.

To enable the reduced diameter portion 64 to bend as described above, it is necessary for the reduced diameter portion to have a diameter sufficiently smaller than the remainder of the shaft, and the reduced diameter portion must be sufficiently long enough to flex without breaking. In particular, the plastic material selected for manufacturing the reduced diameter portion 64 of the shaft is formed of a resilient thermoplastic material and must have a tensile strength which exceeds the tensile stresses placed upon the stretched side of the reduced diameter portion as it rotates during use.

Because the rotating shaft portion 58 exerts forces against the body while it is bent as in FIG. 3, it is also necessary to select a plastic material for the lower neck portion 22 which is flexible yet sufficiently rigid enough to maintain its position once the head portion and upper neck portion are angularly displaced. Thus, once the desired angular displacement of the head portion 26 is achieved, the annular accordion folds 40 of the lower neck portion 22 maintain the angle of displacement during operable rotation of the shaft.

Figure 4:
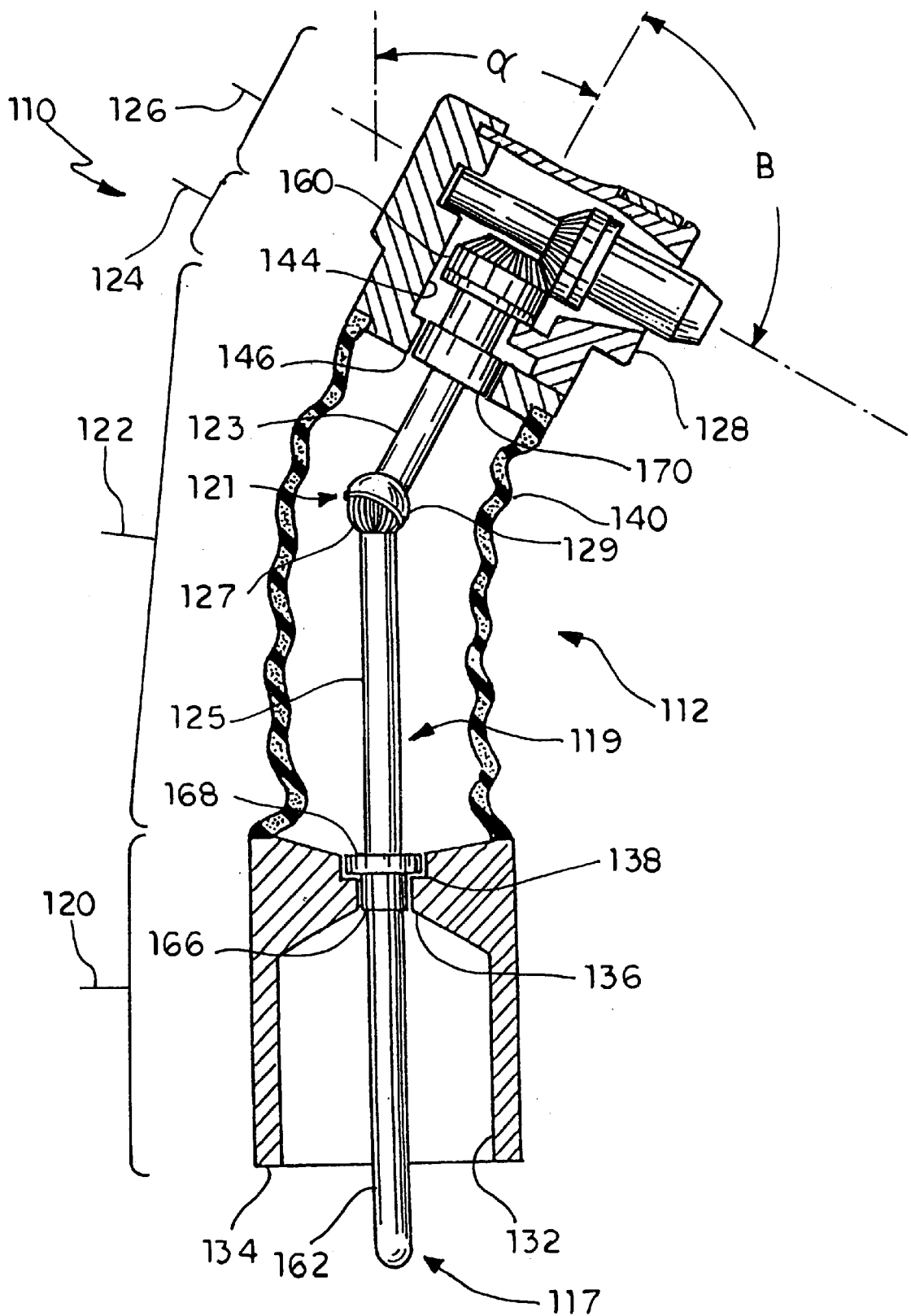
FIG. 4 is a cross sectional view of a second embodiment showing the lower neck portion adjusted by a 30° angle of displacement which causes the universal joint to accommodate the displacement of the upper shaft part relative the lower shaft part.

A second embodiment is illustrated in FIG. 4, where a disposable prophylaxis angle 110 is shown. Because the prophylaxis angle 110 has an identical body 112, identical elements of the first embodiment are indicated by the same reference numeral increased by one hundred. Thus, the body 112 is formed of several distinct sections, generally denoted as a sleeve 120, a lower neck 122, an upper neck 124, and a head 126. As before, a separable cap 128 is removably connected to the head 126. All of the components of the prophylaxis angle 110 are substantially identical to the components described above and shown in FIGS. 2 and 3; therefore, reference is made to the above discussion for similarly labeled components. The only altered feature is the drive gear, generally denoted as 117.

The drive gear 117 generally comprises a shaft portion 119 and a gear portion 160 which is substantially identical to the gear portion 60 of the first embodiment. The shaft portion 119 includes an upper shaft part 123 and a lower shaft part 125. To allow for the angular displacement of the head portion 126, a universal joint 121 is provided between the upper shaft part 123 and the lower shaft part 125. Because the upper shaft part and lower shaft part are substantially rigid, any angular displacement is accommodated by the universal joint 121.

The lower shaft part 125 includes a bottom stem 162, which is disposed to be retained by the collet of a handpiece, and a lower universal gear 127 at the other end of the lower shaft part. Intermediate the lower universal gear 127 and the bottom stem 162 is an enlarged diameter bearing 166 that has an annular flange 168 proximal to the lower universal gear. As before, the bearing 166 contacts a bearing seat 136 for journaled rotation of the lower shaft part at the bearing seat 136. The flange 168 is seated within a shoulder 138 formed into an axial sleeve bore 132, whereby the flange prevents axial displacement of the lower shaft part 125 in the direction of a bottom end 134 of the sleeve portion.

The upper shaft part 123 includes an upper universal gear 129 at one end thereof and a bearing 170 located intermediate the upper universal gear and the gear portion 160. As before, the bearing 170 contacts a bearing seat 146 for journaled rotation of the upper shaft part.

In operation, the disposable prophylaxis angle 110 is capable of similar angular displacement. The lower neck portion 122 is angularly adjustable in any direction for angularly displacing the upper neck bore 144 with respect to the sleeve bore 132. To allow for the desired angular adjustment, the universal joint 121 between the upper shaft part and the lower shaft part of the drive gear 117 accommodates the angular adjustment while maintaining the operative connection between the gear part 160 of the drive gear and the gear part 180 of the driven gear. To selectively adjust the angular displacement of the head portion 126 with respect to the sleeve portion 120, a user should press against the head portion until the desired angle of displacement a is achieved. An angle a between 0°–30° may be achieved in any radial direction such as, for example (as shown in FIG. 4), where the adjustment displaces the upper neck portion and head portion forward 30° with respect to the sleeve portion. As before, it should be apparent that the angle β (between the head portion and the upper neck portion) does not change. When the head portion is angularly displaced, the annular accordion folds 140 allow the lower neck portion 122 to bend in any direction. As before, once the desired angular displacement of the head portion 126 is achieved, the annular accordion folds 140 of the lower neck portion 122 maintain the angle of displacement during operable rotation of the drive gear 117.

It is to be understood that the present invention is not limited to the sole embodiment described above, but encompasses any and all embodiments within the scope of the following claims.

I claim:

1. A disposable prophylaxis angle comprising:

a one-piece body having a sleeve part with an open end, a lower neck part formed of a plurality of annular accordion folds, an upper neck part, and a head part having an axial head bore extending therethrough, said sleeve part having an axial sleeve bore extending therethrough and including a reduced diameter portion forming a lower bearing seat, said upper neck part having an axial upper neck bore extending therethrough and including a reduced diameter portion forming an upper bearing seat, said sleeve bore and said upper neck bore communicating with a passageway extending through said lower neck part, said upper neck bore also communicating with said head bore, said upper neck bore and said head bore being at an angle with respect to each other;

a drive gear including a gear part and a shaft part, said shaft part extending rotatably through said sleeve bore and said upper neck bore, said gear part extending into said head bore, said shaft part including a bottom stem, a bendable reduced diameter section having an upper end and a lower bearing intermediate said bottom stem and said reduced diameter section, said upper end having an upper bearing, said lower bearing engaging said lower bearing seat, and said upper bearing engaging said upper bearing seat;

a driven gear in said head bore operatively connected to said gear part of said drive gear, said driven gear including means for retaining a dental bit;

said lower neck part being angularly adjustable for angularly displacing and maintaining said upper neck bore with respect to said sleeve bore by an angle of displacement, said bendable reduced diameter section of said shaft part accommodating the angular adjustment of said lower neck portion to maintain the operative connection between said gear part of said driven gear and said gear part on said drive gear.

2. The disposable prophylaxis angle according to claim 1, wherein said bendable reduced diameter section is formed of a resilient thermoplastic material having a tensile strength greater than the tensile stresses placed upon said shaft part when said lower neck part is angularly adjusted.

3. The disposable prophylaxis angle according to claim 2, wherein said angle of displacement is between 0°–30° in any direction.

* * * * *